(12) United States Patent
Dhillon et al.

(10) Patent No.: US 10,568,744 B2
(45) Date of Patent: Feb. 25, 2020

(54) IMPLANT PEG WITH MULTIPLE COMPONENTS

(71) Applicant: Wright Medical Technology, Inc., Memphis, TN (US)

(72) Inventors: Braham K. Dhillon, Memphis, TN (US); Daniel E. Free, Arlington, TN (US); Ramon Luna, Arlington, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 0 days.

(21) Appl. No.: 15/559,739

(22) PCT Filed: Oct. 5, 2016

(86) PCT No.: PCT/US2016/055514
§ 371 (c)(1),
(2) Date: Sep. 19, 2017

(87) PCT Pub. No.: WO2018/067143
PCT Pub. Date: Apr. 12, 2018

(65) Prior Publication Data
US 2019/0216610 A1    Jul. 18, 2019

(51) Int. Cl.
*A61F 2/42* (2006.01)
*A61F 2/30* (2006.01)

(52) U.S. Cl.
CPC ........ *A61F 2/4202* (2013.01); *A61F 2/30749* (2013.01); *A61F 2002/30143* (2013.01);
(Continued)

(58) Field of Classification Search
CPC . A61B 17/80; A61B 17/8033; A61B 17/8042; A61F 2/28; A61F 2/2402; A61F 2/30749
See application file for complete search history.

(56) References Cited

U.S. PATENT DOCUMENTS

| | | |
|---|---|---|
| 4,716,893 A | 1/1988 | Fischer et al. |
| 5,441,537 A | 8/1995 | Kenna |

(Continued)

FOREIGN PATENT DOCUMENTS

| | | |
|---|---|---|
| EP | 1433444 B1 | 11/2005 |
| WO | 2006/099270 A2 | 9/2006 |

OTHER PUBLICATIONS

Examination report No. 1 issued in connection with corresponding Australian patent application No. 2016398373, dated Mar. 1, 2018, 8 pages.

(Continued)

*Primary Examiner* — Jason-Dennis N Stewart
(74) *Attorney, Agent, or Firm* — Duane Morris LLP

(57) ABSTRACT

An implant system comprises an implant plate adapted to be positioned on a surface of a resected bone. The implant plate has a plurality of openings. A plurality of independently positionable pegs attach the implant plate to the bone. Each peg has a longitudinal axis and comprises: a peg body and a retaining device. The peg body is inserted into a peg hole in the bone. The peg body has a transverse dimension in a direction normal to the longitudinal axis, the transverse dimension larger than the openings of the plate. The retaining device is separate from the peg body, and is configured to attach to the peg body, with at least a first portion of the retaining device positioned above an upper surface of the implant plate, and a connecting portion of the retaining device extending through one of the openings of the implant plate.

24 Claims, 9 Drawing Sheets

(52) U.S. Cl.
CPC .............. *A61F 2002/30154* (2013.01); *A61F 2002/30156* (2013.01); *A61F 2002/30332* (2013.01); *A61F 2002/30433* (2013.01); *A61F 2002/30594* (2013.01); *A61F 2002/30878* (2013.01); *A61F 2002/4207* (2013.01)

(56) References Cited

U.S. PATENT DOCUMENTS

| | | |
|---|---|---|
| 6,440,135 B2 | 8/2002 | Orbay et al. |
| 7,517,182 B2 | 4/2009 | Cabrele |
| 7,780,711 B2 | 8/2010 | Orbay et al. |
| 8,574,272 B2 | 11/2013 | Wallenstein et al. |
| 9,168,075 B2 | 10/2015 | Dell'Oca |
| 9,295,563 B2 | 3/2016 | Haines |
| 9,345,578 B2 | 5/2016 | Collazo et al. |
| 2001/0007941 A1 | 7/2001 | Steiner et al. |
| 2005/0288792 A1 | 12/2005 | Landes et al. |
| 2006/0041261 A1 | 2/2006 | Osypka |
| 2007/0265629 A1 | 11/2007 | Martin et al. |
| 2008/0021477 A1 | 1/2008 | Strnad et al. |
| 2008/0147203 A1 | 6/2008 | Cronin et al. |
| 2008/0195233 A1 | 8/2008 | Ferrari et al. |
| 2009/0054992 A1 | 2/2009 | Landes et al. |
| 2009/0171396 A1 | 7/2009 | Baynham et al. |
| 2009/0198285 A1 | 8/2009 | Raven, III |
| 2010/0331981 A1 | 12/2010 | Mobarakh |
| 2013/0218284 A1* | 8/2013 | Eickmann ............ A61F 2/389 623/20.34 |
| 2015/0201971 A1 | 7/2015 | Gaines et al. |
| 2015/0305753 A1 | 10/2015 | McGinley et al. |
| 2015/0320567 A1 | 11/2015 | Terrill et al. |

OTHER PUBLICATIONS

Office Action issued in connection with corresponding Canadian patent application No. 2,979,856, dated Jul. 19, 2018, 3 pages.
ACUMED® ACU-LOC® 2—Volar Distal Radius Plating System Surgical Technique, Jan. 2013, 28 pages.
Distal Radius: Flower Orthopedics, 2016, 3 pages.
International Search Report and Written Opinion issued for corresponding International patent application No. PCT/US2016/055514, dated Jul. 5, 2017, 11 pages.
European Search Report issued in connection with corresponding European patent application No. 16893803.3, dated Jul. 9, 2018, 8 pages.

* cited by examiner

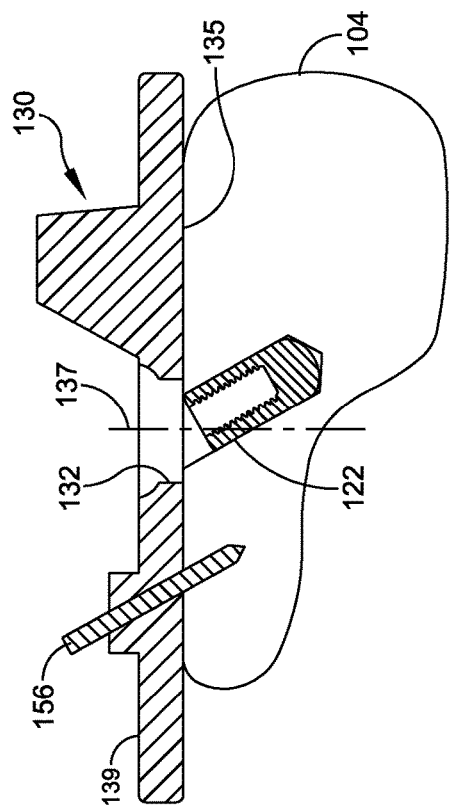
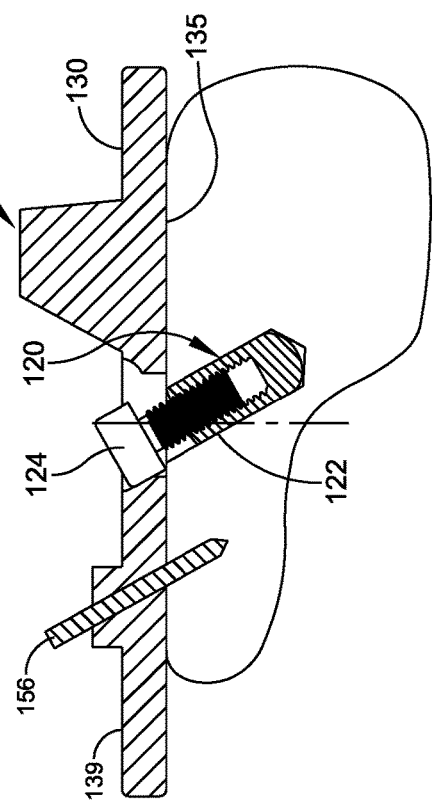
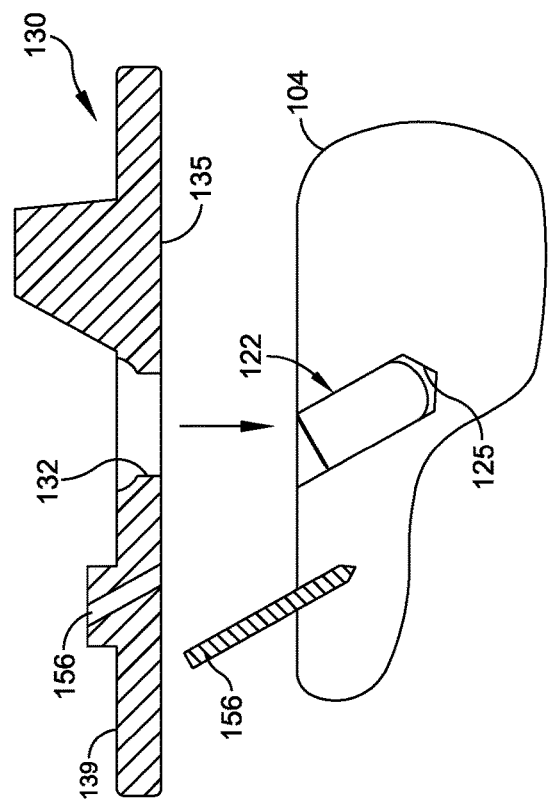
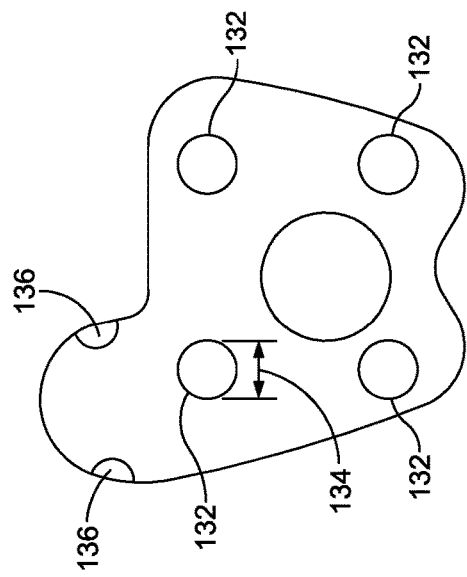

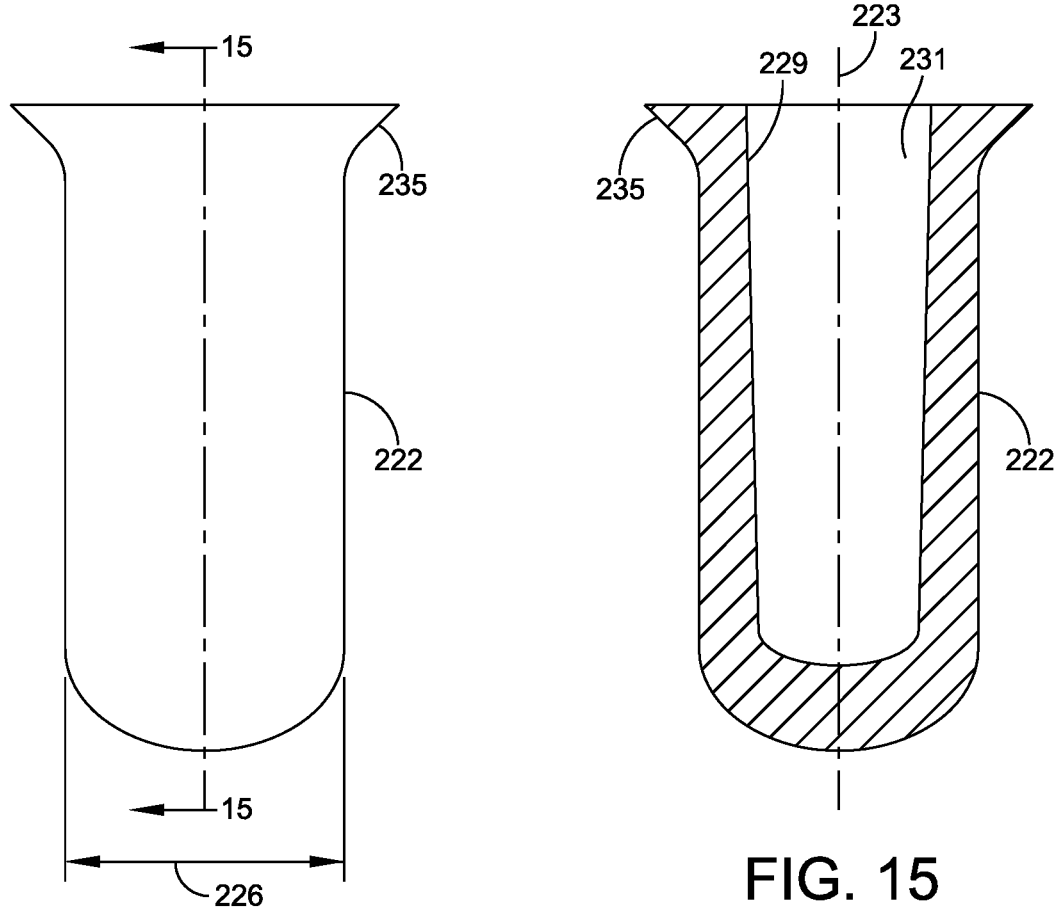
FIG. 14
FIG. 15
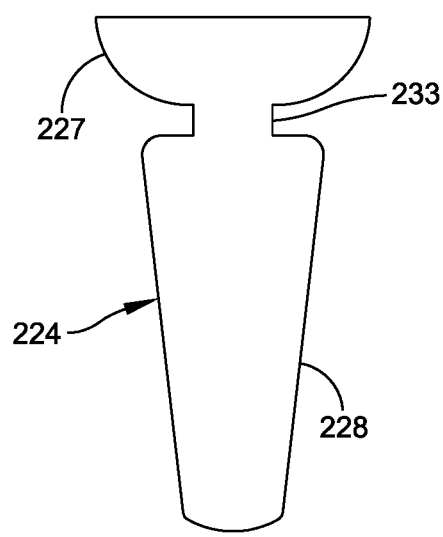
FIG. 16

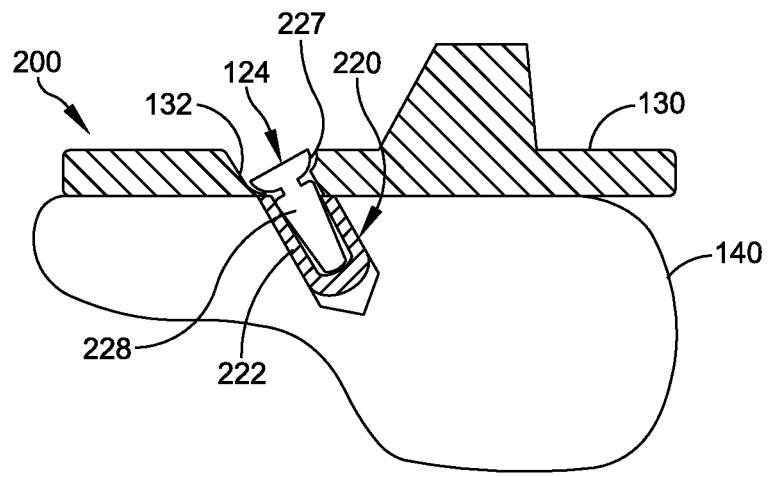
FIG. 17
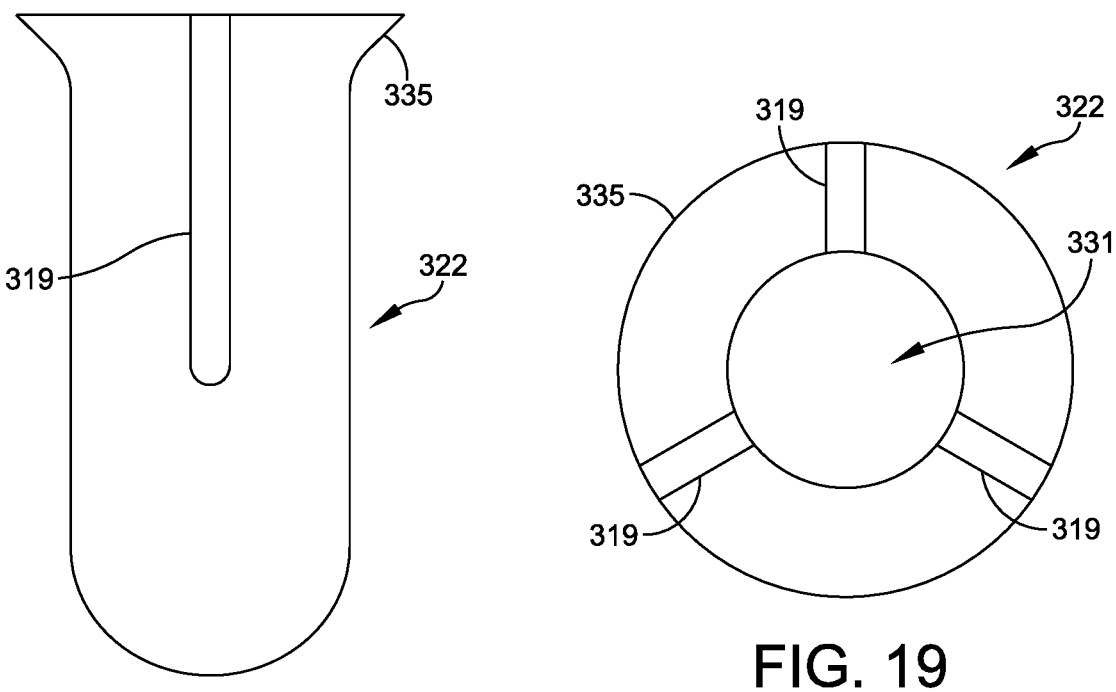
FIG. 18
FIG. 19

US 10,568,744 B2

IMPLANT PEG WITH MULTIPLE COMPONENTS

CROSS REFERENCE TO RELATED APPLICATIONS

This application is a national phase entry under 35 U.S.C. 371 of international patent application No. PCT/US2016/055514, filed Oct. 5, 2016, the entirety of which is incorporated herein by reference.

FIELD

This disclosure relates generally to medical devices, and specifically to bone implants.

BACKGROUND

An ankle joint may become severely damaged and may be treated by total ankle replacement. One type of total ankle replacement comprises two components; one part is implanted in a resected tibia and the other part is implanted in a resected talus. The talar implant can include a stem and/or one or more pegs, screws or combinations of pegs, screws and stem that extend into openings drilled into the resected surface of the bone. In some patients, the quality of the bone into which the pegs are to be inserted is poor.

SUMMARY

In some embodiments, an implant system comprises an implant plate adapted to be positioned on a surface of a resected bone. The implant plate has a plurality of openings therethrough. A plurality of independently positionable pegs are provided for attaching the implant plate to the resected bone. Each peg has a longitudinal axis and comprises: a peg body and a retaining device. The peg body is adapted to be inserted into a respective peg hole in the resected bone. The peg body has a transverse dimension in a direction normal to the longitudinal axis, the transverse dimension larger than the plurality of openings. The retaining device is separate from the peg body. The retaining device is configured to attach to the peg body, with at least a first portion of the retaining device positioned above an upper surface of the implant plate, and a connecting portion of the retaining device extending through one of the openings of the implant plate.

In some embodiments, an implant system comprises an implant plate configured to be positioned on a surface of a resected bone. The implant plate has a plurality of openings therethrough. A plurality of independently positionable pegs are provided for attaching the implant plate to the resected bone. Each peg has a longitudinal axis and comprises: a peg body and a retaining device. The peg body is adapted to be inserted into a respective peg hole in the resected bone. The peg body has a transverse dimension in a direction normal to the longitudinal axis. The transverse dimension is larger than a diameter of at least one of the plurality of openings. The peg body further comprises a proximal connecting portion penetrating one of the openings of the implant plate. The retaining device is separate from the peg body. The retaining device is configured to attach to the peg body, with at least a first portion of the retaining device above an upper surface of the implant plate.

In some embodiments, a method, comprises: (a) drilling at least two peg holes into a resected surface of a bone; (b) assembling at least two pegs to an implant plate, the implant plate having a plurality of openings, each of the two pegs having a longitudinal axis and a peg body with a transverse dimension in a direction normal to the longitudinal axis, the transverse dimension larger than the plurality of openings; and (c) after step (b), attaching the implant to the bone so that the at least two pegs are inserted in the at least two peg holes.

BRIEF DESCRIPTION OF THE DRAWINGS

FIG. 10 is a side view showing the talus of FIG. 9 after insertion of the peg body.
FIG. 11 is a superior view of the talar implant plate of FIG. 1.
FIG. 12 is a side view showing the talus of FIG. 10 after positioning the talar implant plate of FIG. 11 thereon.
FIG. 13 shows the talar implant assembly of FIG. 12 after inserting the retaining devices through holes in the plate and into the peg body.
FIG. 14 is a side view of a peg body according to some embodiments.
FIG. 15 is a cross-sectional view taken along section line 15-15 of FIG. 14.
FIG. 16 shows a retaining device a retaining device suitable for use with the peg body of FIG. 15.
FIG. 17 shows a talar implant assembly including the peg of FIGS. 14-16.
FIG. 18 is a side view of another peg body according to some embodiments.
FIG. 19 is a superior view of the peg body of FIG. 18.

DETAILED DESCRIPTION

Figure 1:
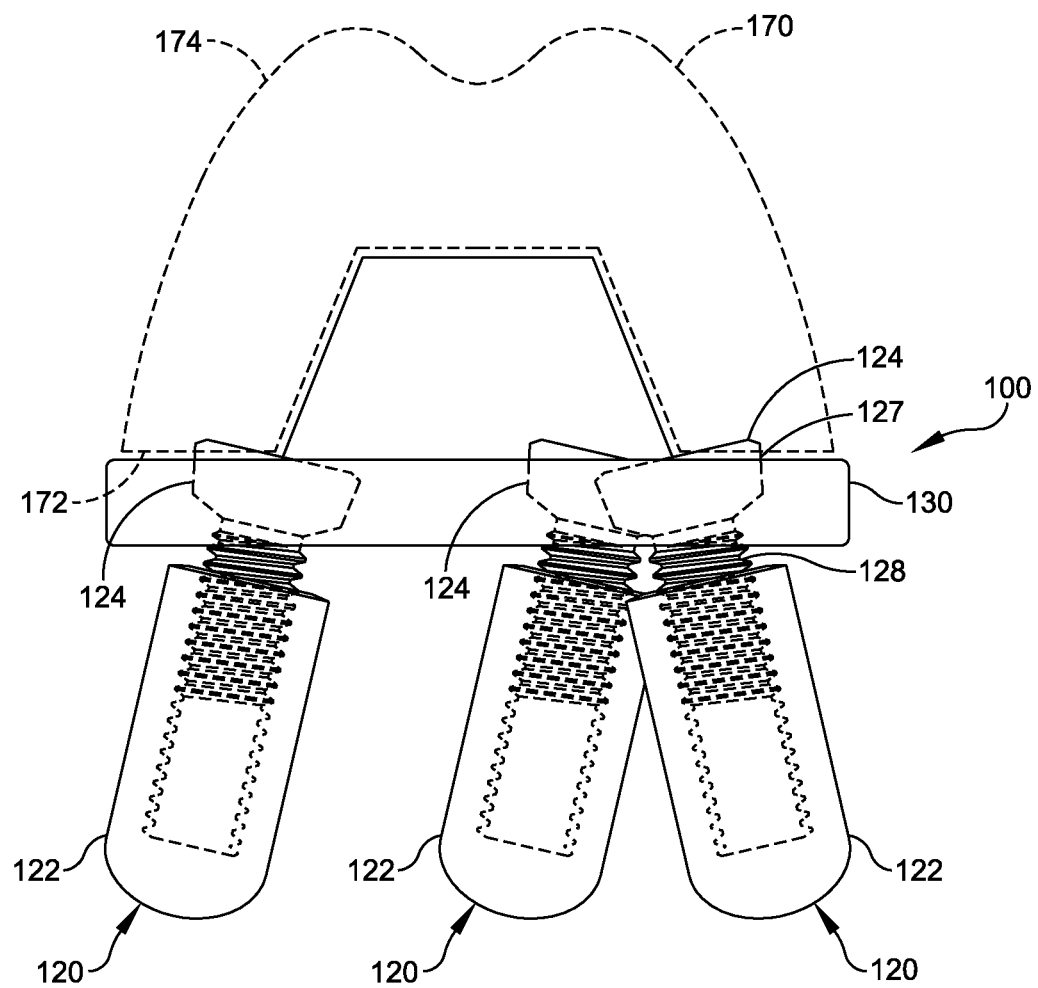
FIG. 1 is an anterior view of a talar implant assembly according to some embodiments.
Figure 2:
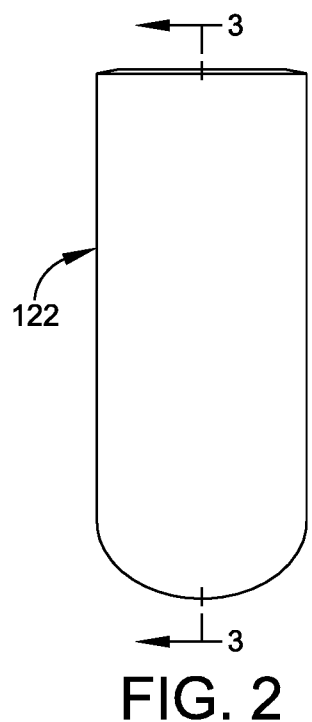
FIG. 2 is a side view of one of the peg bodies of FIG. 1.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

FIG. 1 is a schematic diagram of an exemplary implant system 100 according to some embodiments of this disclosure. In particular, the implant system 100 is a talar plate assembly 100. It should be understood that the implant system 100 may also be referred to herein as the talar plate assembly 100. The exemplary implant system 100 comprises an implant plate 130 and a plurality of independently positionable pegs 120. In some embodiments, the plurality of pegs m include at least two different insertion angles, at least two different peg body lengths, at least two different peg body diameters, or at least two different peg configurations, or any combination of two or more of these features. FIG. 1 also shows (in phantom) a talar dome 170 mounted on the implant plate 130. The talar dome 170 has a mounting surface 172 attachable to the implant plate 130 and an articulating surface 174 opposite the mounting surface 172. The talar plate assembly 100 can be included in a total ankle prosthesis.

The implant plate 130 is configured to be positioned on a surface of a resected bone, such as a resected talus 140. The implant plate 130 has a plurality of peg openings 132 therethrough, as best seen in FIG. 11. The implant plate 130 also has two or more openings 136 for receiving k-wires or pins 156. In some embodiments, as shown in FIG. 11, the openings 136 are at the edge of the plate 130. In other embodiments, the openings 136 are within the perimeter of the plate 130 and are completely surrounded by material of the plate. In other words, the openings 136 are disposed interior to a peripheral edge of the implant plate. In some embodiments, all of the peg openings 132 of the plate 130 have the same diameter. In other embodiments, the peg openings 132 vary in diameter.

The plurality of independently positionable pegs 120 are provided for attaching or securing the implant plate 130 to the resected bone 140. Each peg 120 has a longitudinal axis 123. Each peg 120 comprises a peg body 122 adapted to be inserted into a respective peg hole 125 in the resected bone 140.

Figure 3:
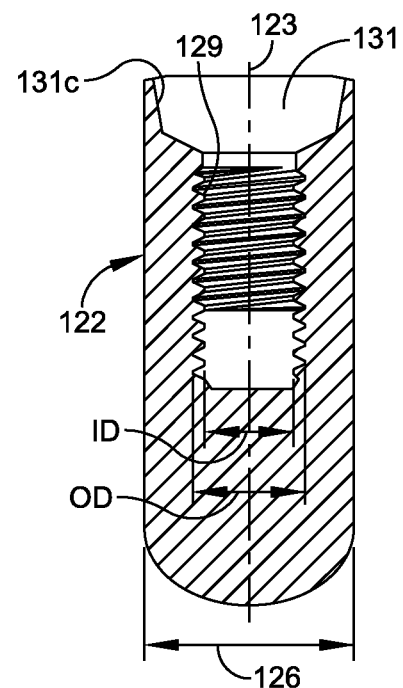
FIG. 3 is a cross sectional view taken along section line 3-3 of FIG. 2.
Figure 4A:
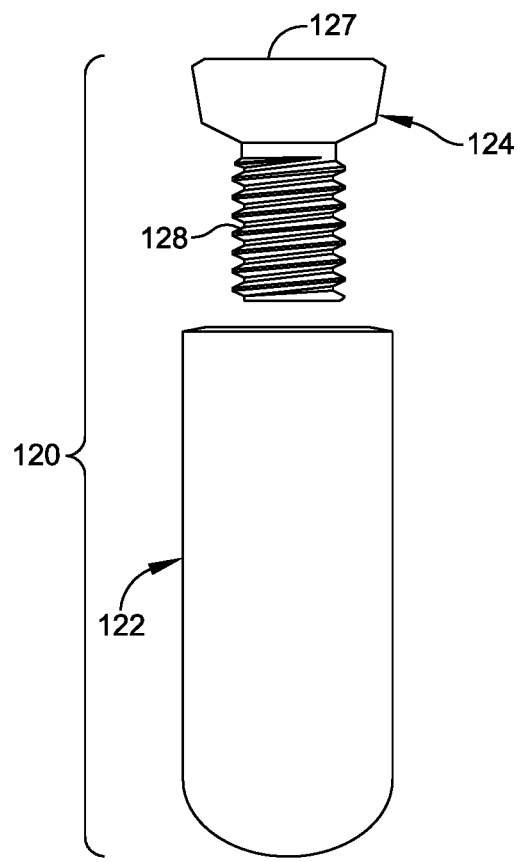
FIG. 4A shows a retaining device as shown in FIG. 1.
Figure 4B:
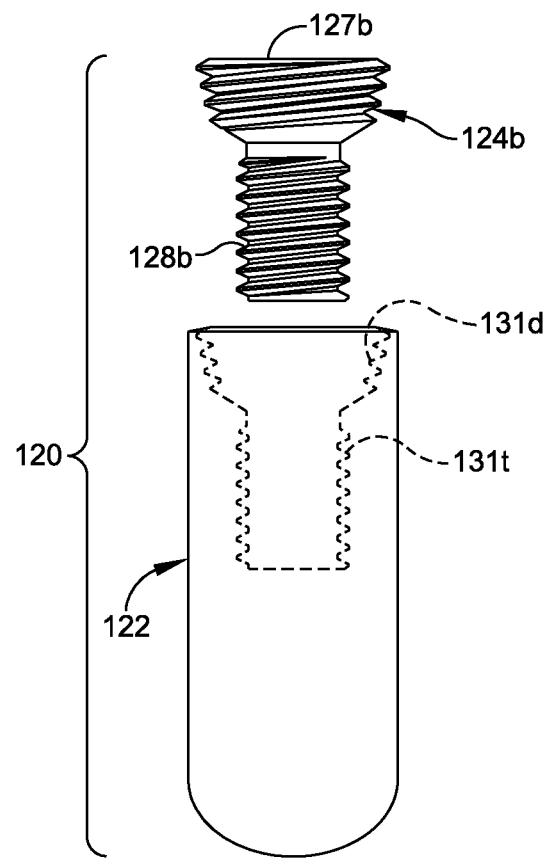
FIG. 4B shows the peg of FIG. 2 with a locking screw as a retaining device.

In some embodiments. the peg body 122 of at least one of the plurality of pegs 120 has a cylindrical portion with an outer diameter 126 greater than an outer diameter 134 of a corresponding one of the plurality of openings 132. Although shown and described as cylindrical, the pegs may be shaped triangular, square, hexagonal, or a combination thereof. The side surface of the peg body 122 can have a textured surface. The peg body 122 has an opening 131 with an inner wall 129 defining an interior cavity along a longitudinal axis 123 of the peg body. In some embodiments, the opening 131 of the peg body 122 has a countersink and/or counterbore or relief pocket 131c for receiving a top portion 127 of a retaining device 124. In some embodiments, the countersink or counterbore 131c has no threads, and is adapted to receive a non-locking screw 124, as shown in FIG. 3. In other embodiments, the countersink or counterbore 131d has threads to engage corresponding threads in a head 127b of a locking screw 124b, as shown in FIG. 4B. In some embodiments, the distal portion 131t of the opening has threads for receiving and engaging threads of a distal portion 128, 128b of a screw. In some embodiments, each peg body 122 has a transverse dimension 126 in a direction normal to the longitudinal axis 123. The transverse dimension 126 is larger than a diameter 134 of at least one of the plurality of openings 132 of the implant plate 130. In some embodiments, the transverse direction is an outer diameter 126 (FIG. 3) of the peg body 122, and the outer diameter 126 of the peg body is larger than the diameter 134 of the openings 132 (FIG. 11) of the implant plate 130.

The peg 120 further comprises a retaining device 124 separate from the peg body 122. The retaining device 124 is configured to attach to the peg body 122, with at least a first portion 127 of the retaining device 124 positioned above a lower surface 135 of the implant plate 130. In some embodiments, the first portion 127 of the retaining device 124 is positioned entirely within the thickness of the implant plate 130, between the lower surface 135 and the top surface 139 to ensure proper seating of the talar dome onto the implant (e.g., talar) plate. In this configuration, the first portion 127 does not protrude above the top surface 139 of the implant plate 130. Countersinks, counterbores or relief pockets on the top surface of the talar plate can allow the first portion 127 of the retaining device to be positioned within the thickness of the implant plate 130. In some embodiments, the first portion 127 of the retaining device 124 is positioned above a lower surface 135 of the plate 130, and can extend slightly above an upper surface 139 of the plate 130. In other embodiments, the first portion 127 of the retaining device 124 is positioned above a upper surface 139 of the plate 130, and a connecting portion 128 of the retaining device 124 extends from the bottom of the countersink 131c—or the top surface 139 of the opening 131 if there is no countersink or counterbore—of the implant plate 130 to the peg body 122.

In some embodiments, the retaining device 124 of at least one of the plurality of pegs 120 is an inner component having a proximal head 127 larger in diameter or periphery than the corresponding one of the plurality of openings 132 (or diameter or inner periphery) and a distal body 128 sized to fit through or be received within the corresponding one of the plurality of openings 132. The distal body 128 of the inner component 124 is configured to engage the inner wall 129 of the opening 131 of the peg body 122. In some embodiments, the distal body 128 has male threads disposed on an outer surface thereof and the inner wall 129 of opening 131 has female threads. For example, the inner wall can be threaded, and the inner component 124 can be a screw. In some embodiments, the inner component is a non-locking screw, as shown in FIG. 4A, or a locking screw as shown in FIG. 4B.

In some embodiments, the distal body 128 has barbs disposed on an outer surface thereof, and the inner wall 129 of the opening 131 can be smooth, ridged, grooved, or barbed. In some embodiments, the distal body 128 has ridges, and the inner wall 129 can be smooth, ridged, grooved, or barbed. In some embodiments, the distal body 128 has splines, and the inner wall 129 can be smooth or splined. In other embodiments, either or both of the distal body 128 and the inner wall 129 can have a knurled surface. In other embodiments, either or both of the distal body 128 and the inner wall 129 can have a tapered surface.

FIGS. 2-4B show components of an exemplary peg assembly 120. In some embodiments, the peg body 122 is rotationally symmetric, and has a circular cross section in any plane, transverse to the longitudinal axis 123 of the peg 120. The peg body 122 is generally bullet-shaped. The side surface of the peg body 122 can have a textured surface. The distal end of the peg body 122 can be hemispherical, ellipsoidal, or the like. FIG. 3 is a cross-sectional view of the peg body 122 taken along section line 3-3 of FIG. 2. The peg body 122 has a central opening 131 with an inner wall 129. The proximal (top) portion of the inner wall 129 can include a countersink and/or counterbore 131c as described above. The distal portion of the inner wall 129 has an outer diameter that is smaller than the diameter 134 of the openings 132 in the implant 130. In some embodiments, the first portion 127 of the retaining device 124 is configured to be positioned entirely within the thickness of the implant plate 130, between the lower surface 135 and the top surface 139 to ensure proper seating of the talar dome onto the talar plate. Countersinks, counterbores or relief pockets on the top surface of the talar plate can allow the first portion 127 of the retaining device to be positioned within the thickness of the implant plate 130. In some embodiments, the first portion 127 of the retaining device 124 is configured to be positioned above a lower surface 135 of the plate 130, and to extend slightly above an upper surface of the plate 130. In other embodiments, the first portion 127 of the retaining device 124 is configured to be positioned above an upper surface 139 of the plate 130, and a connecting portion 128 of the retaining device 124 is configured to be extend through one of the openings 132 from the bottom of the countersink 131c—or the top surface of the opening 131 if there is no countersink or counterbore—of the implant plate 130 to the peg body 122.

In some embodiments, the inner wall 129 has a female thread with an inner diameter ID and an outer diameter OD (shown in FIG. 3), where the outer diameter is smaller than the diameter 134 of the openings 132 in the implant 130. The inner component can be a non-locking screw 124 having a head 127 with a smooth outer sidewall, as shown in FIG. 4A. In other embodiments, the inner component can be a locking screw 124b having a head 127b with a threaded outer sidewall, as shown in FIG. 4B. The distal body 128b of the locking screw 124b can be the same as the distal body 128 of the non-locking screw 124, meaning, the distal body of the non-locking screw 124 and the distal body of the locking screw 124b can both be threaded. In some embodiments, the retaining device 124 is a polyaxial screw, configured for locking at a variety of angles with respect to a longitudinal axis 137 of the holes 132 (shown in FIG. 12). For example, in some non-limiting embodiments, the screws 124 can be inserted at any angle within about 20 degrees of the axis 137. For example, the polyaxial screws can be inserted at angles from about 45, 40, 35, 30, 25, 20, 15, 10, 5, and 0 degrees (°) with respect to the longitudinal axis 137.

Figure 5:
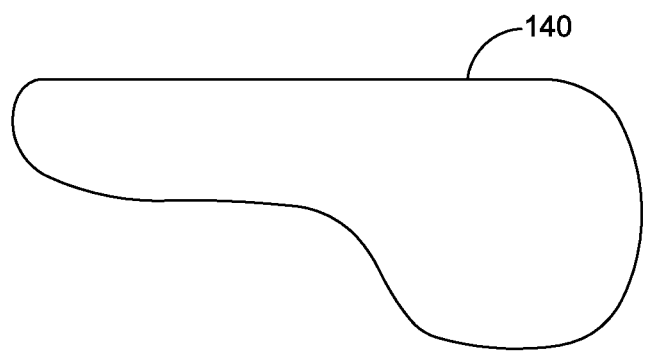
FIG. 5 is a lateral view of a resected talus.
Figure 6:
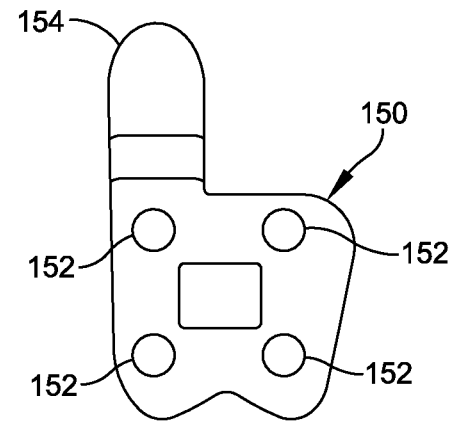
FIG. 6 is a superior view of a talar implant trial for sizing the implant plate of FIG. 1.

FIGS. 5-13 show an exemplary method for implanting the talar plate assembly 100 in a resected talus 140 (FIG. 5). FIG. 5 is a lateral view of the resected talus 140. FIG. 6 shows a talar plate trial component 150 that can be used for sizing the talar plate 130, and locating and drilling a suitable set of peg holes 125 in the resected talus 140. The surgeon moves the talar plate trial component 150 into an optimal position (adjacent the talus) by holding the handle portion 154.

In some embodiments, the final positioning of the talar construct can also be accomplished by the "floating Talus" method. In the "floating Talus" method the surgeon places each of a plurality of trials in the bony spaces between the resected talus and the tibia individually, and moves the ankle joint through its full range of motion. By doing this each trial settle in when it reaches its optimal position, instead of being directed by the surgeon to a predetermined location.

Figure 7:
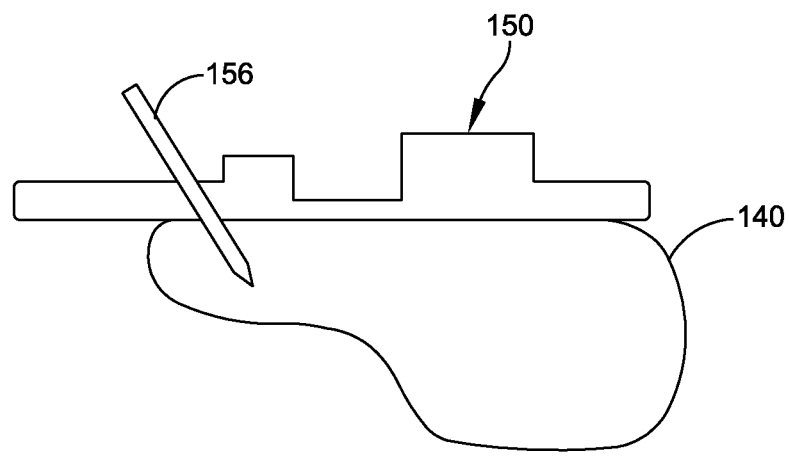
FIG. 7 is a side view of the talar implant trial of FIG. 6 pinned to the resected talus of FIG. 5.

Once the talar plate trial component 150 is properly positioned, the surgeon inserts at least two k-wires or pins 156 through the talar plate trial component 150 into the bone 140, as shown in FIG. 7.

Figure 8:
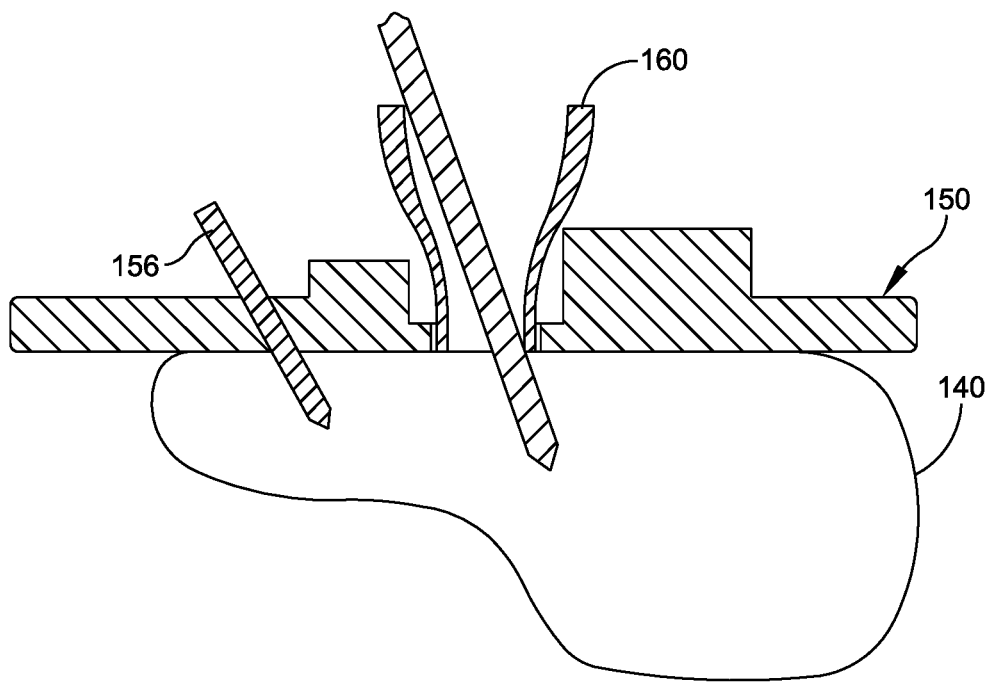
FIG. 8 is a side view showing the pilot hole being drilled in the resected talus using a drill guide and the talar implant trial of FIG. 6.

Pilot holes are then drilled in the resected bone 140 using a drill guide 160 that allows the surgeon to vary the direction and angle of the pilot holes, as shown in FIG. 8. Each peg 120 in the plurality of pegs is adapted to be inserted at a respective angle relative to the implant plate 130, independently from the angle of each remaining peg 120 in the plurality of pegs. Thus, each pilot hole can be drilled at a respective angle relative to the implant plate trial 150, independently from the angle of each remaining pilot hole. Upon drilling each pilot hole, the surgeon can inspect the quality of the bone around that hole, and if the bone quality is poor, the surgeon can fill the pilot hole with a substrate such as bone cement, bone filler, or an autograft or allograft (e.g., synthetic bone fill material), and re-drill the pilot hole at a different angle and/or direction.

Once the pilot holes are all drilled, the surgeon can remove the drill guide 160 and the talar plate trial component 150. The k-wires 156 remain positioned in the bone 140, to enable proper positioning and alignment of the implant plate 130. Then the implant plate 130 is positioned on the resected bone 140, with the k-wires 156 extending through the openings 136 of the implant plate 130.

Then, one of the retaining devices 124 is inserted into its corresponding peg body 122, with at least a first portion of the retaining device 127 positioned above a bottom surface 135 of the implant plate 130, and either a second portion 128 of the retaining device 124 extends to the peg body, or a portion of the peg body penetrates the bottom surface of a respective opening 132 in the implant plate 130. In some embodiments, the first portion 127 of the retaining device 124 is positioned entirely within the thickness of the implant plate 130. In some embodiments, the first portion 127 of the retaining device 124 is positioned above a lower surface 135 of the plate 130, and to extend slightly above an upper surface 139 of the plate 130, between the lower surface 135 and the top surface 139 to ensure proper seating of the talar dome onto the talar plate. Countersinks, counterbores or relief pockets on the top surface of the talar plate can allow the first portion 127 of the retaining device to be positioned within the thickness of the implant plate 130. In other embodiments, the first portion 127 of the retaining device 124 is positioned above an upper surface 139 of the plate 130, and a connecting portion 128 of the retaining device 124 is configured to be extend through one of the openings 132 from the bottom of the countersink 131c—or the top surface of the opening 131 if there is no countersink or counterbore—of the implant plate 130 to the peg body 122.

Figure 9:
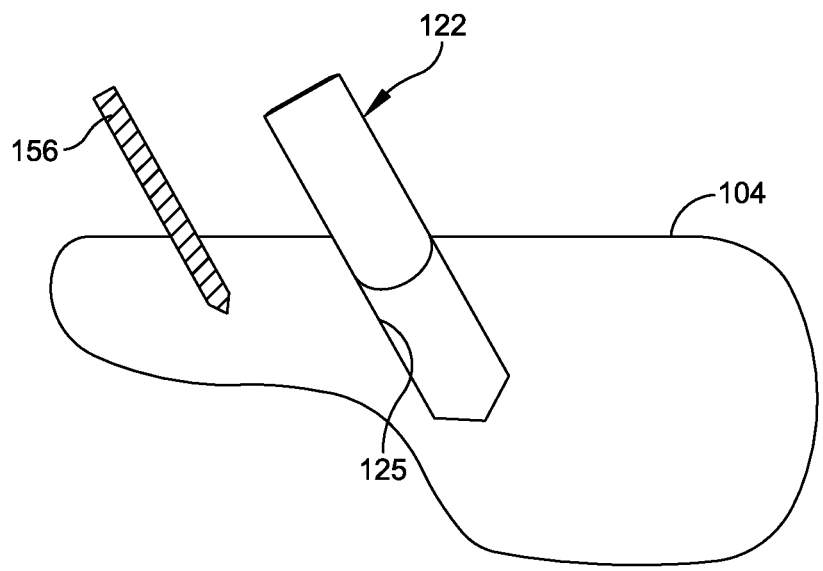
FIG. 9 is a side view showing insertion of the peg body of FIG. 2 into the talus of FIG. 8.

As shown in FIGS. 9 and 10, in some embodiments of the method, the peg bodies 122 are inserted in the peg holes 125 before assembling the pegs to the implant plate 130. In the case where the pegs 120 or peg bodies 122 are implanted at respectively different angles, the surgeon may wish to position the peg 120 or peg body 122 first within the talus, then position the implant plate 130 on the resected talus, aligning the holes 136 of the plate 130 with the k-wires 156, which results in the holes 132 of the implant plate 130 being aligned over the proximal portions of the pegs 120 or peg bodies 122. Then the surgeon inserts the inner components 124 into the peg bodies 122 from above the plate 130. (In other embodiments, discussed below with respect to FIGS. 20-22, a proximal end 443 or 552 of the peg body 422 or 522 extends into or through the plate 130, and an outer component 447 or 553 is placed over the proximal end.)

FIG. 11 is a dorsal view of the implant plate 130, including the openings 132 and the k-wire openings 136. FIG. 12 is a lateral view of the bone 140 with the implant plate 130 inserted on the resected surface of the bone, positioning the plate 130 using the k-wires or pins 156. The implant plate 130 is positioned on the resected talus with the k-wires 156 extending through the openings 136 in the implant plate 130. The retaining devices 124 are inserted from the top side of the plate 130, through each of the openings 132 and into the peg bodies 122, which have previously been positioned in the peg holes 125 in the embodiment of FIG. 11. The retaining devices 124 attached the peg bodies 122 to the plate 130. The top portion 127 of the retaining device 124 extends above the bottom surface 135 of the plate 130. In some embodiments, the top portion 127 of the retaining device 124 extends above the upper surface 139 of the plate.

In an embodiment of the method as shown in FIGS. 9-12, each peg body 122 is positioned independently, and then the implant plate 130 is positioned and each retaining device 124 is driven into the peg body 122 from the top side of the implant plate 130. In some situations, this approach may give the surgeon flexibility and ease in fitting and driving each individual peg body 122 into the bone 170. Each peg can be individually sized, fitted and inserted. FIG. 13 is a lateral cross-sectional view of the implant plate assembly 100 after implantation. After implanting the implant plate assembly 100, the talar dome 170 (FIG. 1) is attached to the implant plate 130.

In other embodiments of the method, using a "back table" approach, the surgeon or staff pre-assembles the pegs 120 to the bone 170, forming the implant plate assembly 100 as shown in FIG. 1 before the plate 130 is positioned on the resected bone 170. If the pegs 120 are assembled in the back table approach, all of the pegs are oriented with their axes at the same angle relative to the bottom surface 135 of the plate 130, and all the peg holes 125 are drilled at the same angle. The retaining devices 124 are inserted through the openings 132 of the implant plate 130 and into each of the threaded distal portions 131t of inner walls 129 of the opening 131. The pegs 120 are driven into position in the peg holes 125 by tapping on the fastening devices 124/124b until the peg bodies 122 are completely seated within their respective peg holes 125.

In some embodiments, the outer diameter of the threads of the distal body 128 is larger than the outer diameter of the threads in the inner wall 129 of opening 131, so that inserting the distal body 128 entirely into the opening 131 of the peg body 122 exerts a force in the radial direction, causing the peg body 122 to strain or expand slightly in the radial direction and securely grip the bone 170. The strain of the peg body 122 can be enhanced if the peg body has radial slots (shown in FIGS. 18-19) extending downward from a top surface of the peg body.

FIGS. 14-17 show another example of a peg 220 according to some embodiments. FIGS. 14-15 show the peg body 222 of peg 220. The peg body 222 of at least one of a plurality of pegs 220 has a cylindrical portion with an outer diameter 226 greater than an outer diameter 134 of a corresponding one of the plurality of openings 132 in the implant plate 130. In some embodiments, each peg body 222 has a transverse dimension 226 in a direction normal to the longitudinal axis 223. The transverse dimension 126 is larger than a diameter 134 of at least one of the plurality of openings 132 of the implant plate 130.

The peg body 222 is rotationally symmetric, and has a circular cross-section in any plane transverse to the longitudinal axis 223 of the peg 220. The peg body 222 is generally bullet-shaped. In other embodiments, the peg body 22 can be various shapes including but not limited to triangular, hexagonal, square, elliptical, and the like. The side surface of the peg body 222 can have a textured surface. The distal end of the peg body 222 can be hemispherical, ellipsoidal, or the like. FIG. 15 is a cross-sectional view of the peg body 222 taken along section line 15-15 of FIG. 14. The peg body 222 has a central opening 231 with an inner wall 229. The inner wall 229 defines an interior cavity along a longitudinal axis 223 of the peg body 222.

A retaining device 224—separate from the peg body 222—is configured to attach to the peg body 222, with at least a first portion 227 of the retaining device 224 positioned above a bottom surface 135 of the implant plate 130 as discussed above, and a connecting portion 233 of the retaining device 224 extending from the proximal portion 227 of the retaining device to the peg body 222. In some embodiments, the first portion 227 of the retaining device 224 is configured to be positioned entirely within the thickness of the implant plate 130, between the lower surface 135 and the top surface 139 to ensure proper seating of the talar dome onto the talar plate. Countersinks, counterbores or relief pockets on the top surface of the talar plate can allow the first portion 227 of the retaining device to be positioned within the thickness of the implant plate 130. In some embodiments, the first portion 227 of the retaining device 224 is configured to be positioned above a lower surface 135 of the plate 130, and to extend slightly above an upper surface 139 of the plate 130. In other embodiments, the first portion 227 of the retaining device 224 is configured to be positioned above an upper surface 139 of the plate 130, and a connecting portion 233 of the retaining device 224 is configured to be extend through one of the openings 132 from the bottom of the countersink 131c—or the top surface of the opening 131 if there is no countersink—of the implant plate 130 to the peg body 222.

In some embodiments, the retaining device 224 of at least one of the plurality of pegs 220 is a unitary inner component having a proximal head 227 larger than the corresponding one of the plurality of openings 132, such that the proximal head 227 is not received within the opening 231, and a distal body 228 sized to fit through the corresponding one of the plurality of openings 132. The distal body 228 of the inner component 224 is configured to engage the inner wall 229 of the opening 231 of the peg body 222. In some embodiments, the distal body 228 a tapered outer surface, and the inner wall 229 of opening 231 has a tapered inner surface. For example, the taper can be a Morse taper. In other embodiments, other tapers are used. In some embodiments, a narrow connecting portion 233 connects the head 227 and the distal body 228. In other embodiments, the connecting portion 233 is as wide as the greatest transverse dimension of the tapered portion 224, for greater strength.

FIG. 17 shows an implant assembly 200 including the implant plate 130, the peg body 222 and the retaining device 224. As in the case of the implant assembly 100 of FIGS. 1-13, if the largest diameter of the distal body 228 and the connecting portion is smaller than the diameter of the openings 132 in the implant plate, the implant plate assembly 200 can be implanted. First each peg body 222 is inserted into its respective peg hole, then the plate 130 is positioned on the resected talus 140, and then the retaining devices 224 are driven into the central opening 231 of each peg body 222.

Alternatively, the implant plate assembly 220 can be pre-assembled using the back table method discussed above, and all the pegs of the assembly inserted into the bone 170 at the same time. Briefly, the implant plate assembly 220 is connected to the pegs 220 and the entire assembly is positioned within and thereon the talus simultaneously.

In some embodiments, the retaining device 224 is unitary. In other embodiments, the retaining device 224 has two components: the bottom component includes the tapered portion 228 and the connecting portion 233, which can have a male outer thread (not shown). The top portion includes a threaded hub or cap screw 227 with a female inner thread (not shown). If the top portion 227 is a separate piece from the bottom portion 228, then the diameter of the bottom portion 228 can be greater than the diameter of the holes 132 of the implant plate 130.

FIGS. 18 and 19 show a variation of the tapered peg body 322. The tapered peg body 322 is the same as the peg body 222, except that a plurality of radial slots 319 extend downward from the top surface of the peg body 322. The tapered slots 319 extend from the inner surface or wall of the peg body 322 to the outer, exterior surface of the peg body 322 (full thickness slots). The tapered slots 319 allow the top of the peg body 335 to deflect slightly in the radial direction when the inner component 224 (retaining device) is inserted into the tapered opening 331 of the peg body 322. Other aspects of the structure and method of FIGS. 18-19 are the same as discussed above with respect to FIGS. 14-17.

Figure 20:
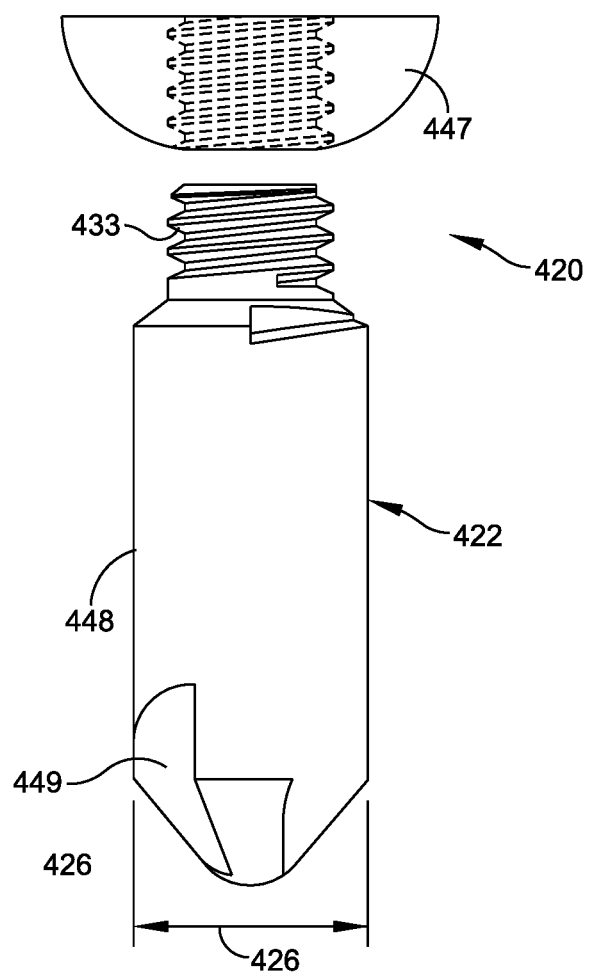
FIG. 20 is an exploded view of an exemplary peg according to some embodiments.
Figure 21:
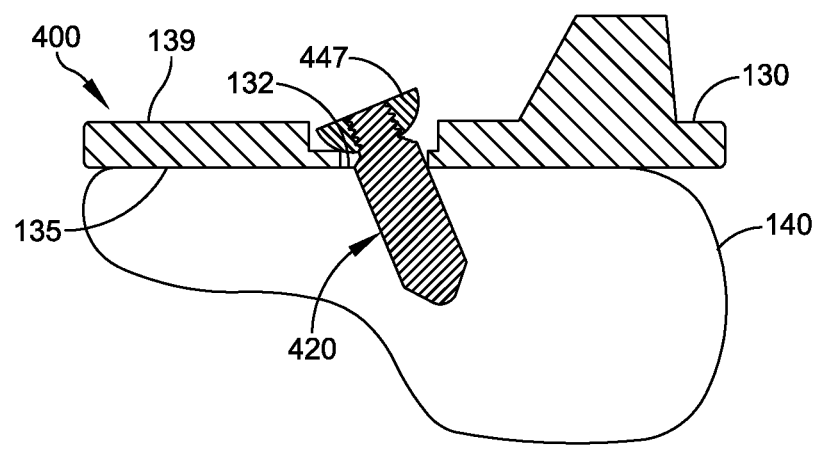
FIG. 21 shows a talar implant assembly including the peg of FIG. 20.

FIGS. 20 and 21 show another exemplary implant plate assembly 400. The assembly 400 has an implant plate 130 and a plurality of independently positionable pegs 420. Each peg 420 has a peg body 422 and a retaining device 447. The peg body 422 is adapted to be inserted into a respective peg hole in the resected bone. The peg body 422 has a transverse dimension 426 in a direction normal to the longitudinal axis of the peg body. The transverse dimension 426 is larger in diameter than the plurality of openings 132 of the implant plate. In some embodiments, the retaining device 447 is positioned within the thickness of the implant plate 130, above the bottom surface 135, between the lower surface 135 and the top surface 139 to ensure proper seating of the talar dome onto the implant plate 130 (e.g., talar plate). Countersinks, counterbores or relief pockets on the top surface of the implant plate 130 can allow the retaining device 447 to be positioned within the thickness of the implant plate 130. For example, the retaining device 447 can fit in the countersink or counterbore 131c of the opening 132 in the plate 130. In other embodiments, the retaining device 447 is positioned above an upper surface of the plate 130, and a connecting portion 433 of the peg body 422 extends from the bottom surface 135 of the plate at least part way through the thickness of the plate 130. The transverse dimension 426 is at a central portion of the peg body 422. In some embodiments, the peg body 422 is round and the transverse dimension is a diameter of the peg body. In other embodiments, the peg body has gripping features 449, such as edges that grip bone and resist rotation of the peg body 422 if a torque is applied to the peg body 422. The side surface 448 of the peg body 422 can have a textured surface. For example, the surface can be rough or knurled, and can have barbs, or ridges. The peg body 422 can be solid, without any cavity or opening.

The peg body 422 further comprises a proximal connecting portion 433 configured to extend through one of the openings 132 of the implant plate 130 from a bottom surface 135 of the implant plate 130. For example, in some embodiments, the peg body 422 has a thread on at least the connecting portion 433 of the peg body, and the retaining device is a threaded cap 447 configured to engage the thread of the connecting portion 433 when the thread extends through the corresponding one of the plurality of openings 132. Each of the plurality of openings 132 of the implant plate 130 is configured to receive the connecting portion 433 of the peg body 422 at a plurality of different angles. For example, the pegs can be attached at a variety of angles from about 45, 40, 35, 30, 25, 20, 15, 10, 5, and 0 degrees (°) with respect to a direction normal to the bottom surface 135 of the implant plate 130. Each peg 420 in the plurality of pegs is adapted to be inserted at a respectively different angle relative to the implant plate 130, independently from the angle of each remaining peg in the plurality of pegs.

A retaining device 447 is separate from the peg body 422. The retaining device 447 is configured to attach to the peg body 422, with at least a first portion of the retaining device 427 above a bottom surface 135 of the implant plate 130. In some embodiments, the retaining device 447 is entirely contained between the top surface 139 and the bottom surface 135 of the plate 130. In other embodiments, the retaining device 447 is partially contained between the top surface 139 and the bottom surface 135 of the plate 130, and a portion of the retaining device 447 extends above the top surface 139. In some embodiments, as shown in FIG. 21, the peg body 422 of at least one of the plurality of pegs 420 has a cylindrical portion 448 with a diameter 426 greater than a diameter of a corresponding one of the plurality of peg holes 132; the connecting portion 433 of the peg body 422 of the at least one of the plurality of pegs is a threaded member, the threaded member having an outer diameter smaller than a diameter of a corresponding one of the plurality of openings 132, and the retaining device 447 of the at least one of the plurality of pegs comprises a threaded cap configured to engage the threaded member 433 when the threaded member extends at least partially through the corresponding one of the plurality of openings 132. An implant plate assembly 400 as shown in FIGS. 20-21 can be implanted using the back table method discussed above, in which the pegs 420 are pre-assembled to the implant plate 130 before implanting the pegs in the peg holes.

In other embodiments, ridges, grooves, or barbs can be substituted for the male threads on the member 433, and the corresponding retaining device 447 has ridges, grooves, or barbs substituted for the female threads.

Figure 22:
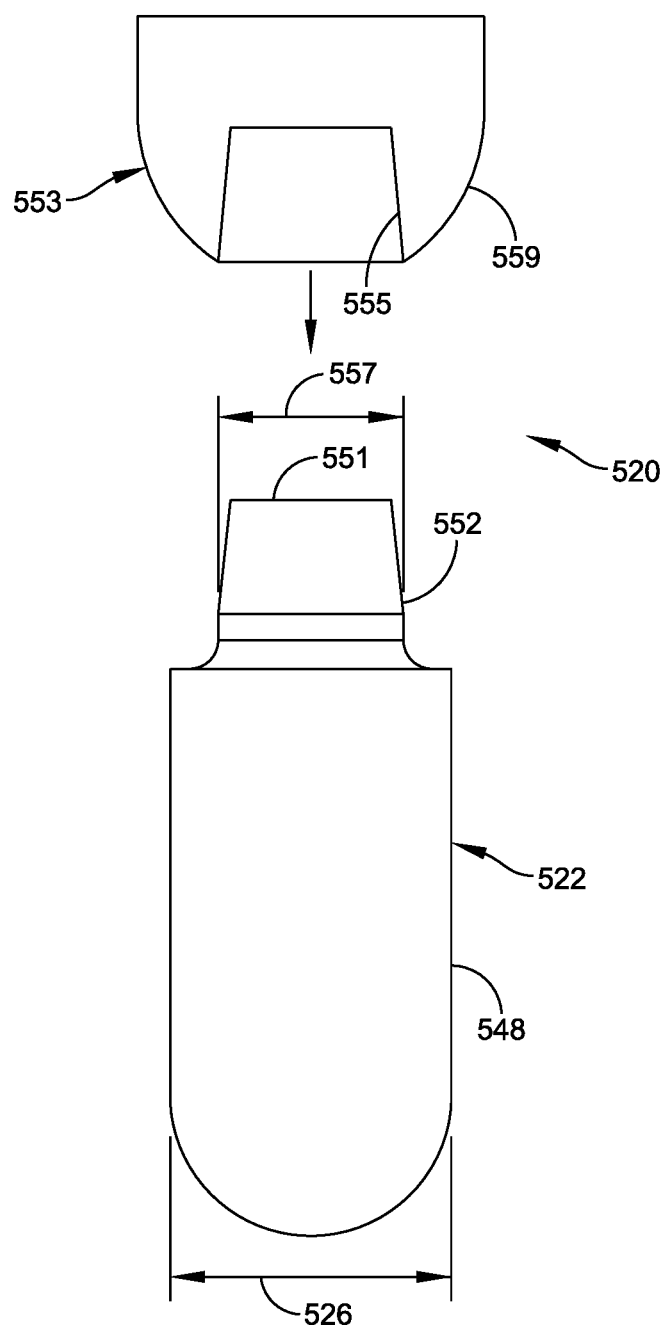
FIG. 22 is a side view of an exemplary peg according to some embodiments.

FIG. 22 shows an example of another peg 520 according to some embodiments. The peg body 522 has a bottom portion 548, which is generally bullet-shaped. The peg body 522 has a transverse dimension (e.g., diameter) 526 in a direction normal to the longitudinal axis (not labelled) of the peg body. The transverse dimension 526 of each peg body 522 is larger than its corresponding opening 132 in the implant plate 130. In some embodiments, all the pegs 522 have the same diameter 526, in other embodiments, the diameters 526 vary from peg to peg. The transverse dimension 526 is at a central portion of the peg body 522. In some embodiments, the peg body 526 has gripping features, such as a textured surface, which can be rough or knurled, and can have barbs, or ridges. The peg body 522 can be solid, without any cavity or opening.

The connecting portion 551 of the peg body 522 of at least one of the plurality of pegs 520 has a tapered outer surface 552, the tapered outer surface 552 having a maximum outer diameter 557 smaller than a diameter 134 of a corresponding one of the plurality of openings 132 in the implant plate 130. The retaining device 553 of the peg 520 comprises a tapered inner surface 555 configured to engage the tapered outer surface 552 when the tapered outer surface 552 extends at least partially through the corresponding one of the plurality of openings 132 of the implant plate 130. The tapered member 551 is inserted through the implant 130 and into the tapered inner surface 555 of the retaining device 553 to form a taper joint such as a Morse taper joint. In some embodiments, the retaining device 553 has a curved outer edge 559 at a bottom end thereof, to allow the angle of the longitudinal axis of the peg body 522 to vary relative to the upper surface 139 of the implant plate 130.

Although the subject matter has been described in terms of exemplary embodiments, it is not limited thereto. Rather, the appended claims should be construed broadly, to include other variants and embodiments, which may be made by those skilled in the art.

What is claimed is:

1. An implant system, comprising:
   an implant plate adapted to be positioned on a surface of a resected bone, the implant plate having a plurality of openings therethrough;
   a plurality of independently positionable pegs for attaching the implant plate to the resected bone, each peg having a longitudinal axis and comprising:
   a peg body adapted to be inserted into a respective peg hole in the resected bone, the peg body having a transverse dimension in a direction normal to the longitudinal axis, the transverse dimension larger than the plurality of openings, and
   a retaining device separate from the peg body, the retaining device configured to attach to the peg body, with at least a first portion of the retaining device positioned above an upper surface of the implant plate, and a connecting portion of the retaining device extending therethrough.

2. The implant system of claim 1, wherein:
   the peg body of at least one of the plurality of pegs has a cylindrical portion with an outer diameter greater than an outer diameter of a corresponding one of the plurality of openings, the peg body having an inner wall defining an interior cavity along a longitudinal axis thereof, and
   the retaining device of the at least one of the plurality of pegs is an inner component having a proximal head larger than the corresponding one of the plurality of openings and a distal body sized to fit through the corresponding one of the plurality of openings, the body of the inner component configured to engage the inner wall of the peg body.

3. The implant system of claim 2, wherein the inner wall is threaded, and the inner component is a screw.

4. The implant system of claim 2, wherein the inner wall has a taper and the outer peg body has a corresponding taper.

5. The implant system of claim 4, wherein the taper is a Morse taper.

6. The implant system of claim 4, wherein the outer peg body has a plurality of radial slots extending downward from a top of the outer peg body, so that the outer peg body is adapted to deflect radially when the inner component is inserted into the outer peg body.

7. An implant system, comprising:
   an implant plate configured to be positioned on a surface of a resected bone, the implant plate having a plurality of openings therethrough;
   a plurality of independently positionable pegs for attaching the implant plate to the resected bone, each peg having a longitudinal axis and comprising:
   a peg body adapted to be inserted into a respective peg hole in the resected bone, the peg body having a transverse dimension in a direction normal to the longitudinal axis, the transverse dimension larger than a diameter of at least one of the plurality of openings, the peg body further comprising a proximal connecting portion penetrating one of the openings of the implant plate, and
   a retaining device separate from the peg body, the retaining device configured to attach to the peg body, with at least a first portion of the retaining device above an upper surface of the implant plate.

8. The implant system of claim 7, wherein the transverse dimension is at a central portion of the peg body.

9. The implant system of claim 8, wherein the transverse dimension is a diameter of the peg body.

10. The implant system of claim 7, wherein each of the plurality of openings is configured to receive a second portion of the retaining device or the connecting portion of the peg body at a plurality of different angles.

11. The implant system of claim 10, wherein and each peg in the plurality of pegs is adapted to be inserted at a respective angle relative to the implant plate, independently from the angle of each remaining peg in the plurality of pegs.

12. The implant system of claim 10, wherein the implant plate is a talar plate adapted to be positioned on a surface of a resected talus.

13. The implant system of claim 7, wherein each peg in the plurality of pegs is adapted to be positioned at a respectively different angle.

14. The implant system of claim 7, wherein the peg body of the at least one peg has a textured surface on a portion thereof.

15. The implant system of claim 7, wherein the peg body has a thread on at least the connecting portion of the peg body, and the retaining device is a threaded cap configured to engage the thread of the connecting portion when the thread extends through the corresponding one of the plurality of openings.

16. The implant system of claim 7, wherein:
    the peg body of at least one of the plurality of pegs has a cylindrical portion with a diameter greater than a diameter of a corresponding one of the plurality of peg holes,
    the connecting portion of the peg body of the at least one of the plurality of pegs is a threaded member, the threaded member having an outer diameter smaller than a diameter of a corresponding one of the plurality of openings, and
    the retaining device of the at least one of the plurality of pegs comprises a threaded cap configured to engage the threaded member when the threaded member extends through the corresponding one of the plurality of openings.

17. The implant system of claim 7, wherein:
    the connecting portion of the peg body of the at least one of the plurality of pegs has a tapered outer surface, the tapered outer surface having a maximum outer diameter smaller than a diameter of a corresponding one of the plurality of openings, and
    the retaining device of the at least one of the plurality of pegs comprises a tapered inner surface configured to engage the tapered outer surface when the tapered outer surface extends through the corresponding one of the plurality of openings.

18. The implant system of claim 17, wherein the tapered outer surface and the tapered inner surface form a Morse taper joint.

19. The implant system of claim 7, further comprising a talar dome having a mounting surface attachable to the implant plate and an articulating surface opposite the mounting surface.

20. The implant system of claim 7, wherein the plurality of pegs includes at least one of the group consisting of:
   at least two different peg body lengths,
   at least two different peg body diameters, or
   at least two different peg configurations.

21. A method, comprising:
   (a) drilling at least two peg holes into a resected surface of a bone;
   (b) assembling at least two pegs to an implant plate, the implant plate having a plurality of openings, each of the two pegs having a longitudinal axis and a peg body with a transverse dimension in a direction normal to the longitudinal axis, the transverse dimension larger than the plurality of openings
   (c) inserting a screw through the implant and into the peg body of at least one of the at least two pegs; and
   (d) attaching the implant to the bone so that the at least two pegs are inserted in the at least two peg holes.

22. The method of claim 21, wherein each peg has a retaining device, and step (b) includes attaching the one of the peg bodies to the retaining device, with at least a first portion of the retaining device positioned above the implant plate, and either a second portion of the retaining device or a portion of the peg body penetrating a respective opening in the implant plate.

23. The method of claim 21, wherein step (b) includes inserting a tapered member through the implant and through the peg body of at least one of the at least two pegs to form a Morse taper joint.

24. The method of claim 21, wherein step (b) includes joining a threaded cap above the implant to a threaded member of the peg body extending through the implant plate.

* * * * *